United States Patent [19]

Cenedella

[11] Patent Number: 4,628,116

[45] Date of Patent: Dec. 9, 1986

[54] VINYL BROMIDE EXTRACTION OF BUTYRIC ACID AND BUTANOL FROM MICROBIAL FERMENTATION BROTH

[76] Inventor: Richard J. Cenedella, Rte. 1, Box 28, Kirksville, Mo. 63501

[21] Appl. No.: 519,974

[22] Filed: Jan. 8, 1986

[51] Int. Cl.$^4$ .................. C07C 29/86; C07C 31/12; C07C 51/48; C07C 53/124

[52] U.S. Cl. .................. 562/513; 435/141; 435/150; 435/151; 435/160; 435/163; 435/165; 435/832; 435/842; 568/918

[58] Field of Search .................. 562/513, 606, 608; 568/918, 840; 435/141, 160, 136, 140, 832, 842

[56] References Cited

U.S. PATENT DOCUMENTS 1,405,055 1/1922 McDermott et al. .................. 562/513
4,260,836 4/1981 Levy .................. 568/918
4,282,323 8/1981 Yates .................. 562/513

Primary Examiner—Vivian Garner
Attorney, Agent, or Firm—Zarley, McKee, Thomte, Voorhees & Sease

[57] ABSTRACT

The process of extracting butyric acid and normal butanol from microbial fermentation broth, comprising contacting an aqueous solution of a microbial fermentation broth with vinyl bromide to extract any butyric acid and normal butanol which is present from the fermentation broth into the vinyl bromide. The vinyl bromide is thereafter separated from the aqueous fermentation broth and then evaporated, leaving the butyric acid and/or normal butanol in substantially pure, isolated form.

7 Claims, 1 Drawing Figure

VINYL BROMIDE EXTRACTION OF BUTYRIC ACID AND BUTANOL FROM MICROBIAL FERMENTATION BROTH

BACKGROUND OF THE INVENTION

In recent times, there have been considerable investigations of alternative fuel sources to those derived from petroleum crude. One such area of investigation has included alcohols and certain organic acids such as butyric acid. Butyric acid and normal butanol are potential fuel sources available from fermentation of carbohydrate containing industrial materials such as municipal solid waste, waste paper, distressed grain, agricultural crop residue such as corn cobs and the like, and other such fermentation substrates. For example, butanol fermentation takes place in the presence of butanol forming bacterium such as Clostridium acetobutylicum (Weizmann). This invention relates to the use of aqueous microbial fermentation broths which contain small percentages of butyric acid and butanol. The primary objective of the invention is to extract the butyric acid and butanol from the microbial fermentation broth in an efficient energy manner.

Such fermentation broths may typically contain from about 0.2% up to about 1% by weight of each of normal butyric acid and normal butanol. For effective and efficient use, the butyric acid and butanol must be extracted and concentrated. It goes without saying that the extraction and the concentration must be in a manner which is efficient and itself not high energy consuming. For example, if tremendous amounts of energy are consumed in the extraction any energy efficiency from the alternative fuel source is simply consumed in the preparation, making the net balance negative. Thus, it is not feasible to employ a process which is highly efficient for separation purposes, but one which uses an amount of energy at least equal to or greater than the amount of energy theoretically available from the extracted butyric acid and/or butanol.

This invention has as its primary objective a means of efficiently and in a low energy manner, extracting butyric acid and butanol from microbial fermentation broths.

Another objective of the present invention is to efficiently and in a low energy manner extract butyric acid and butanol from microbial fermentation broths by use of vinyl bromide as the extracting solvent.

Another objective of the present invention is to provide a highly efficient extraction unit operation for maximizing the efficiency of vinyl bromide extraction of butyric acid and butanol from aqueous fermentation broth.

A yet further objective of the present invention is to provide an efficient and cost effective process utilizing vinyl bromide in a column extraction process for the recovery of butyric acid and normal butanol from microbial fermentation systems.

A yet further objective of the present invention is to develop an extraction system for extracting butyric acid and normal butanol from microbial fermentation broths which is far superior and more efficient than the extraction of butanol from such broths by use of Freon 11 as disclosed in Levy, U.S. Pat. No. 4,260,836, issued Apr. 7, 1981.

The means and manner of accomplishing each of the above objectives as well as others, will become apparent from the detailed description of the invention which follows hereinafter.

SUMMARY OF THE INVENTION

In accordance with this invention, an aqueous microbial fermentation broth containing butyric acid and/or normal butyl alcohol is first acidified to a pH within the range of from about 4.0 down to about 3.5; and, thereafter, the acidified fermentation broth is introduced into the bottom of a series of extraction columns containing vinyl bromide. Aqueous fermentation broth, being lighter than the vinyl bromide floats naturally to the top of the column, wherein it is drawn off. Any butyric acid and/or normal butyl alcohol that is present in the microbial fermentation broth is extracted into the vinyl bromide which remains in the column. Thereafter, the column is drawn down, the vinyl bromide evaporated, and the result is a residue of substantially pure butyric acid and/or normal butanol.

DETAILED DESCRIPTION OF THE INVENTION

Figure 1:
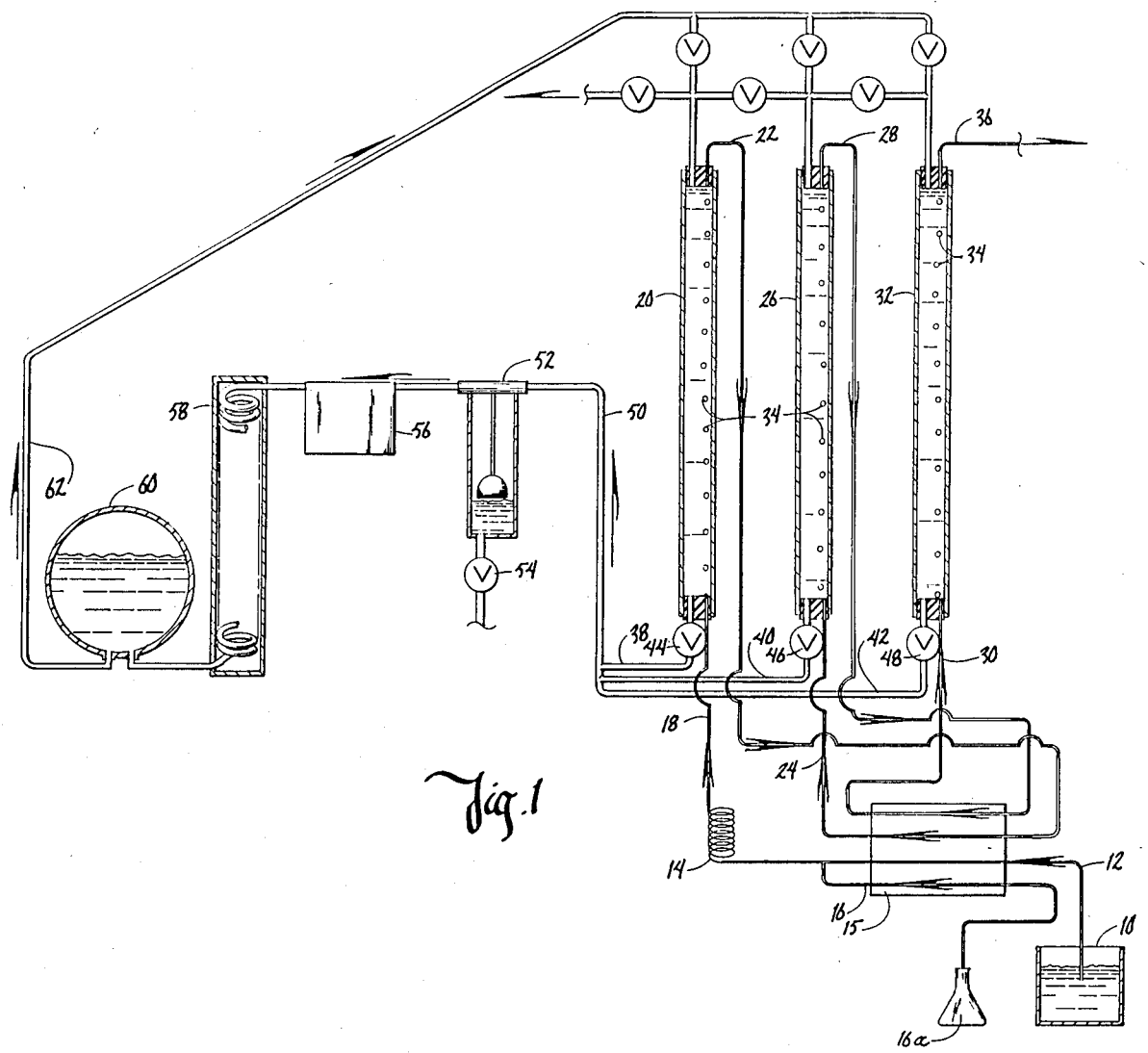
FIG. 1 is a schematic of continuous column extraction system useful in performing the process of this invention.

The art of making butyric acid and/or butanol by fermentation is known. The process for making those by fermentation was discovered by Charles Weizmann, after whom the fermenting organism is named, Clostridium acetobutylicum (Weizmann). Fermentation processes for the production of butanol are known and described in detail in much published literature and a number of patents. Since the butanol fermentation is known, the details of a representative process need not be described in detail herein. For examples of patents discussing butanol fermentation processes, see for example, the following U.S. Pat. Nos. 2,223,788; 2,218,426; 2,377,197; 2,202,785; 4,205,133; 1,875,536; 2,147,487; 2,260,126 and 2,182,989. Each of the butanol fermentation processes and apparatus discussed in these representative state of the art patents, can be used for formation of the fermented butanol useful in this invention. And so, the disclosures of these patents, to the extent that they disclose representative fermenting processes useful for preparation of butanol from bacterium such as Clostridium acetobutylicum (Weizmann), are incorporated herein by reference.

As those skilled in the fermentation art know, butanol produced by a fermentation process, such as those mentioned in the above patents, can be purified to produce pure butanol, or an alcohol product mixture can be separated and used. The product mixture which can be separated is predominantly butanol, but does have small amounts of fermentation by-products such as butyric acid, ethanol and acetone. In accordance with the process of this invention, either the purified butanol may be used, or the fermentation butanol, without separating the fermentation by-products. And so, "microbial fermentation broth" as used herein, refers to a mixture of butanol, butyric acid, acetone and ethanol, which is predominantly butanol and butyric acid.

Briefly, a low cellulose value waste material such as spent grain mashes, molasses, municipal solid waste, waste paper, wood chips, distressed grain, agricultural crop residue such as corn stalks, cobs, straw, bagasse and the like, are suitable carbohydrate containing fermentables useful as the substrate for the butanol production. The fermentable substrate material is mixed with butanol forming bacterium such as *Clostridium acetobutylicum* (Weizmann), or others such as *Clostridium saccharo acetobutylicum*, described in U.S. Pat. No. 2,089,522 of Woodruff, et al; the bacteria of the group *Clostridium inverto acetobutylicum*, described in U.S. Pat. No. 2,089,562 of Legg, et al; *Clostridium saccharo acetobutylicum-gamma*, described in U.S. Pat. No. 2,050,219 of Arzberger; the bacteria of the group *Clostridium propyl butylicum*, the bacteria of the group *Clostridium saccharo-butyl-acetonicum-liquefaciens*, described in U.S. Pat. No. 2,139,108, issued Dec. 6, 1938; and *Clostridium saccharo-butyl-acetonicum-liquefaciens-gamma and Clostridium saccharo-butyl-acetonicum-liquefaciens-delta*, described in U.S. Pat. No. 2,139,111 issued Dec. 6, 1938 and *Bacillus butacone* described in U.S. Pat. No. 2,147,487, issued Feb. 14, 1939.

The invention is generally applicable to any bacteria of this butanol forming class, but the starch fermenting bacteria *Clostridium acetobutylicum* (Weizmann) or the *Bacillus butacone*, which is relatively insensitive to the presence of air during fermentation is preferred.

The amount of butanol forming bacterial culture employed can vary from ½% to 10%, preferably from 3% to 7.5% by weight of the fermentable mash and suitable results, for example, can be achieved with a 5% innoculation of the active culture. Suitable fermenting conditions include: maintenance at fermenting temperatures of 20° C. to 40° C., preferably 25° C. to 35° C. in the presence of well-known bacteria nutrients such as nitrates, acetates, sulfates and the like, at a pH within the range of 5.0 to 6.5 for from 10 hours to 48 hours, preferably 18 to 36 hours.

The fermented butanol may then be separated by conventional chemical separation techniques such as filtration with filter fermenters such as those described in U.S. Pat. No. 4,205,133, the disclosure of which is incorporated herein by reference. As previously mentioned, the butanol may be used in the form of fermented butanol, or it may be purified to provide pure butanol. However, since the fermented butanol works substantially as well as the purified butanol, there is economic advantage in using the fermented butanol, which is therefore preferred.

The microbial fermentation broth, prepared in one of the typical manners mentioned hereinbefore, is now ready for extraction of the butyric acid and normal butanol that is present. As heretofore mentioned, typically the amount of butyric acid and butanol present will vary somewhat, depending upon the precise microbial fermentation that is performed, but generally the amount of each will range up to about 1% by weight of the fermentation broth.

It has now been discovered, surprisingly, that the vinyl bromide possesses a combination of characteristics which render it ideal for the efficient and cost effective recovery of butyric acid, normal butanol, and other similar products from aqueous microbial broths resulting from fermentation systems as heretofore described. The combination of conditions which make vinyl bromide a superior extraction solvent for use in the technique of this invention, include among others, the following: butyric acid and normal butanol readily partition into vinyl bromide from aqueous systems. Vinyl bromide possesses a very low heat of evaporation. Vinyl bromide has low solubility in water. Vinyl bromide is resistant to the formation of emulsions. Finally, vinyl bromide has other desirable characteristics such as low flammability and comparatively low toxicity.

Speaking first in general terms of the overall process of this invention, the microbial fermentation broth containing butyric acid and normal butanol, is contacted with vinyl bromide. This extracts the butyric acid and/or normal butanol that is present from the aqueous microbial fermentation broth into the vinyl bromide extract. Thereafter, the vinyl bromide extract containing the butyric acid and/or normal butanol is separated from the microbial fermentation broth. The separation is very easy to perform in view of the fact that the vinyl bromide is considerably more dense than the aqueous fermentation broth and as a result, the broth will readily float up through a vinyl bromide column. The vinyl bromide itself will boil at about 15° C. and thus under vacuum can be brought to boil considerably easier than other solvents of low energy consumption. Upon boiling, the vinyl bromide evaporates, leaving behind a residue of substantially pure isolated butyric acid and/or normal butanol. More details of the process will be given later in connection with the reference to the extraction unit shown in the schematic drawing. However, there are certain conditions for the extraction worthy of mention first.

It is important in conducting the process of this invention, that the fermentation broth first has its pH adjusted to an acid level of 4 or less, and preferably within the range of 3.5 to 4.0. This is necessary to convert salts of butyric acid, which are insoluble in vinyl bromide, to free butyric acid, which is soluble in vinyl bromide. It is preferred that a mineral acid be employed and the most preferred mineral acid is hydrochloric acid. There is no particular advantage to using a more acid pH than 3.5 and thus the lower pH range of 3.5 is a practical lower limit.

The process does not appear to be temperature dependent and can be run successfully over a range of from about 4° C. up to about 15° C. Temperatures above 15° C. should be avoided, since vinyl bromide itself will boil at 15.6° C.

Turning next to the drawing, it can be seen that a vessel containing microbial fermentation broth 10 is brought into communication with a mixing coil 14 via line 12 via peristaltic pump 15. A source of a mineral acid, typically hydrochloric acid, depicted at 16a is also in communication with mixing coil 14, via line 16. The fermentation broth and the hydrochloric acid are mixed in a sufficient amount to provide an overall pH of 3.5 and then introduced via line 18 into extraction column 20. Extraction column 20 is filled with vinyl bromide solvent. It has an outline 22 which is in communication with an inlet line 24 with a second extraction column 26, which in turn has an outlet line 28 in communication with an inlet line 30 and yet another like extraction column 32.

Thus, it can be seen that in the drawing there is depicted a series of extraction columns connected in seriatum, 20, 26 and 32. Each is filled with vinyl bromide, and each is connected in such a manner that the outlet from one may be passed as the inlet into the second in the series and so on. The amount of columns in this series can vary from about three to about eight, depending upon the extraction efficiency one desires. The preferred number of columns will be from about four to about seven.

The fermentation broth is introduced into the bottom of each column through the action of a small pump 15, for example, via line 18 into column 20. This aqueous fermentation broth has a specific gravity about equal to water. The vinyl bromide has a specific gravity of about 1.51. As a result, the aqueous fermentation broth will pass upwardly through the column, floating to the top as depicted via bubbles 34. As the broth passes upwardly through each of the columns, for example, column 20, the vinyl bromide extracts the butanol and butyric acid in a preferential manner away from the fermentation broth. Thus, the broth that leaves column 20 via line 22 will be somewhat depleted in butyric acid and normal butanol content. Conversely the broth that leaves the second column, that is, column 26, will be even more depleted, and likewise, the broth that leaves the third column, column 32, will be even more depleted. After the broth leaves the third column as depicted via line 36, it is substantially depleted of butyric acid and normal butanol, and is removed to storage for other processings.

Each of the columns 20, 26 and 32, has a drain line, 38, 40 and 42 with suitable valves 44, 46 and 48, positioned thereon. Valve 44, 46 and 48 can be opened to drain the vinyl bromide from each of the columns into drain line 50. Placed on drain line 50 is a product trap 52. Product trap 52 is nothing more than a vacuum distillation system. In product trap 52, a slight vacuum is maintained on the vinyl bromide. As a result, because of its low boiling point, the vinyl bromide boils, and instantly evaporates away, leaving behind a residue of butyric acid and normal butanol which may be taken off of the product trap via line 54. The evaporated vinyl bromide is then directed to compressor 56 and condenser coil 58 for recondensation to the liquid level. It may then be stored in storage tank 60 and re-introduced via line 62 into the top of each of columns 20, 26 and 32. It therefore can be seen that a continuous system can be employed, with renewed vinyl bromide extraction solvent being fed into the top of each of the columns at the same rate that extracted solvent is drawn off at the bottom.

A suitable pump, such as a peristaltic pump, representatively depicted at 15, can be utilized for pumping of mineral acid and fermentation broth into the mixing coil 14 and then into the bottom of column 20 via line 18.

The following examples are offered to further illustrate the process of this invention, and to illustrate the efficiency of vinyl bromide as a superior solvent system over fluorocarbon systems such as Freon 11. In each of the examples below, it is to be understood that the system just previously described in connection with the drawing was employed. The pH in every instance was adjusted to about 3.5 using hydrochloric acid, because at a pH of 3.5, 95% of the butyric acid present is present as the free acid, and therefore is quite soluble in vinyl bromide. The percolation rate of the acidified fermentation broth up through each of the columns was at a rate of 2.9 milliliters per minute The columns contained a volume of either 70 or 90 milliliters of vinyl bromide. The fermentation mixture was collected at the top of the columns and passed through the additional columns in the series of three.

The concentration of butyric acid and normal butanol in the aliquots of the fermentation broth was measured by gas chromatographic analysis. The extraction temperatures ranged between 4° C. and 15° C. as specified in the experiments.

The vinyl bromide was collected and passed through a compressor fitted with a trap. The vinyl bromide was recovered after passage of the vinyl bromide vapors through the cooling coils and the product of the fermentation was recovered in the traps.

In each of the examples, unless otherwise specified, the aqueous fermentation broth employed were either 600 or 1000 milliliter aliquots of a broth from Bacillus sp. fermentation of cheese whey which was acidified from pH 5.9 to pH 3.5 with concentrated HCL.

EXAMPLE 1

The purpose of this example is to compare the ability of vinyl bromide and Freon 11, to extract butyric acid and normal butanol from fermentation broth under standard conditions.

In this example, a single 70 milliliter aliquot of fermentation broth was percolated in sequence through separate columns of vinyl bromide or Freon 11 (each column containing 70 milliliter of the respective solvent). The temperature of extraction was 4° C. The initial concentration of butyric acid in the fermentation broths was measured and found to be 0.703 (g/100 ml). The normal butanol concentration was measured and found to be 0.062 (g/100 ml).

Table I shown below, shows the results of extraction of butyric acid from the fermentation broth by sequential extraction with vinyl bromide. Similar results are shown for Freon 11. The results shown in the table are cumulative percent extracted of butyric acid:

TABLE I

| | Cumulative % Extracted | | |
|---|---|---|---|
| | Pass 1 | Pass 2 | Pass 3 |
| Vinyl bromide | 29% | 51% | 65% |
| Freon 11 (CCl$_3$F) | 25% | 44% | 57% |

It can be seen that at 4° C. butyric acid was more readily extracted from fermentation systems by use of vinyl bromide than Freon 11. That is to say, more butyric acid was extracted by vinyl bromide than Freon 11. Three passes of the fermentation broth through the separate columns of vinyl bromide at 4° C. resulted in removal of about 65% of the total butyric acid, and while not shown in the table, about 60% of the normal butanol originally present in the broth.

EXAMPLE 2

The primary objective of this example is to determine the number of times a given volume of vinyl bromide and Freon 11 could be used before the solvent's ability to extract butyric acid and normal butanol is exhausted.

Three separate 70 milliliter volumes of the fermentation broth were percolated through the same 70 milliliter batch of vinyl bromide, or Freon 11. The temperature of the extraction was 4° C. The initial concentration of butyric acid in the product was 0.756 and the initial concentration of normal butanol was 0.058. Table II shows the results for butyric acid.

TABLE II

| | Pass 1 | Pass 2 | Pass 3 |
|---|---|---|---|
| Vinyl bromide | 36% | 29% | 25% |
| Freon 11 | 27.5% | 19% | 14% |

It can be seen that for butyric acid, as represented in Table II, the efficiency of the extraction of butyric acid, once removed by a single pass through an equal volume of vinyl bromide solvent, decreased sharply after each pass. However, the amount of decrease, in other words, the rate of decay of the solvent, was less with vinyl bromide than Freon 11. This indicates superiority of vinyl bromide in that larger percentages of butyric acid were removed for extraction with vinyl bromide and the rate of decay in efficiency of the extraction was less than for Freon 11.

Similar results are shown in Table II-A for n-butanol.

TABLE II-A

| (n-butanol for Example 2) | | | |
|---|---|---|---|
| | Pass 1 | Pass 2 | Pass 3 |
| Vinyl bromide | 27.5% | 18.5% | 14% |
| Freon 11 | 23% | 15% | 6% |

It can be seen that for normal butanol, vinyl bromide is likewise more efficient than Freon 11.

EXAMPLE 3

The purpose of this experiment is to compare the ability of vinyl bromide with that of other organic solvents to extract butyric acid and normal butanol from microbial fermentation broth.

In this example, separate 70 milliliter aliquots of fermentation broth were percolated through a single column containing 70 milliliter of vinyl bromide, Freon 11, carbon disulfide, chloroform, diethylether, and hexane. Because the density of diethylether and hexane are both less than one, the fermentation broth was introduced at the top, rather than the bottom of the column in these extractions. Each solvent was tested at least twice. The results are shown in Table III.

TABLE III

| Comparison of Various Organic Solvents in the Column Extraction of Butyric Acid and n-Butanol from Fermentation Broth, Conducted at 4° C. | | |
|---|---|---|
| | Percent Extracted by a Single Pass[a,b] | |
| | Butyric Acid | n-butanol |
| Vinyl Bromide | 32.4 ± 2.0 | 26.3 ± 3.9 |
| Freon 11 | 26.4 ± 0.6 | 21.9 ± 1.3 |
| Carbon Disulfide | 11.1 (13.2, 9.0) | 17.4 (23.2, 11.7) |
| Chloroform | 35.6 (34.9, 36.3) | 41.3 (39.3, 43.4) |
| Diethylether[c] | 35.8 (34.1, 37.5) | 41.3 (37.3, 45.3) |
| Hexane[c] | 10.6 (14.5, 6.8) | 12.0 (14.6, 9.5) |

[a]Separate 70 ml aliquots of fermentation broth were percolated through a column containing 70 ml of the various solvents.
[b]Values are the mean ± s.e.m. of six separate tests or the average of two tests (individual values in parenthesis).
[c]Reverse percolation was used with these solvents; i.e., the fermentation broth was introduced at the top of the column.

It can be seen that a higher percentage of butyric acid and normal butanol were extracted from the fermentation broth by vinyl bromide than by Freon 11, carbon disulfide or hexane. Chloroform and diethylether provided efficiencies equal to vinyl bromide; however, the higher water solubility and high heat of evaporation of both chloroform and ether limit their practical use in an industrial process. Furthermore, diethyl ether is highly flammable and potentially explosive.

EXAMPLE 4

The objective of this example is to determine the influence of temperature upon the column extraction of butyric acid and normal butanol from fermentation broth by vinyl bromide and Freon 11.

Separate 90 milliliter aliquots of fermentation broth were adjusted to pH 3.5 and percolated through a three column extraction system as shown in the drawing. Each of the columns were filled with approximately 90 milliliter of vinyl bromide or Freon 11. Water at 10° C. or 15° C. was aspirated from a reservoir by vacuum through the outer jacket surrounding each of the columns. Concentration of butyric acid and normal butanol in the fermentation broth was measured by gas chromatographic analysis, both before and after percolating through the three columns of solvent.

Table IV below shows the influence of temperature upon the column extractions of butyric acid from fermentation broth by vinyl bromide and Freon 11. Likewise, Table IV-A shows the influence of temperature upon the extraction of normal butanol from fermentation broth by vinyl bromide and Freon 11.

TABLE IV

| Influence of Temperature upon Extraction of Butyric Acid from Fermentation Broth by Vinyl Bromide and Freon 11 | | |
|---|---|---|
| | % Total Butyric Acid Removed (3 Extractions)[a,b] | |
| Temperature | Vinyl Bromide | Freon 11 |
| 4° C. | 63.8 ± 1.9 | 58.1 ± 0.6 |
| 10° C. | 63.5 ± 3.4 | 52.1 ± 2.0 |
| 15° C. | 72.1 ± 3.5 | 49.7 (48.6) (50.8) |

[a]Samples (90 ml) of fermentation broth (acidified to pH 3.5) were percolated through 3 columns connected in series which were each filled with approximately 90 ml of either vinyl bromide or Freon 11. The initial concentration of butyric acid in the fermentation broth averaged 0.70 g/100 ml. The results are the average of three experiments or in one case two (Freon 11 at 15° C., individual values in parenthesis).
[b]The column extraction system shown in the drawing was used.

TABLE IV-A

| Influence of Temperature Upon the Column Extraction of n-Butanol from Fermentation Broth by Vinyl Bromide and Freon 11 | | |
|---|---|---|
| | % Total n-Butanol Removed (3 Extractions)[a,b] | |
| Temperature | Vinyl Bromide | Freon 11 |
| 4° C. | 60.4 ± 2.7 | 45.5 ± 1.7 |
| 10° C. | 65.2 ± 4.6 | 46.3 ± 3.1 |
| 15° C. | 72.2 ± 3.8 | 48.8 (48.8) (48.8) |

[a]Extraction conducted as described in footnotes to Table 4. The initial concentrations of n-butanol in the fermentation broth averaged 0.07 g/100 ml.
[b]Column extraction system shown in the drawing was used.

From this example, it can be seen that at all temperatures examined, vinyl bromide extracted more butyric acid and normal butanol than Freon 11. In addition, percolation of fermentation broth through three columns of vinyl bromide reacted in series resulted in removal of from 65% to 70% of the total butyric acid and normal butanol. Only 45-50% of each product was removed by Freon 11 under identical conditions. It also can be seen that generally only slightly higher recovery of products were obtained at higher temperatures. The entire range of temperatures was operable, with temperatures approaching 15° C. presenting some degree of greater efficiency.

Therefore, it can be seen that the invention accomplishes at least all of its stated objectives.

What is claimed is:

1. A process of extracting butyric acid and n-butyl alcohol from microbial fermentation broth, containing the same, said process comprising:

contacting an aqueous solution of a microbial fermentation broth having a pH of about 4.0 or less, and containing butyric acid and/or n-butanol with vinyl bromide at a temperature from about 4° C. to about 15° C. to extract said butyric acid and/or said n-butanol from said fermentation broth into said vinyl bromide, separating said vinyl bromide from said broth, and separating said butyric acid and/or said n-butanol from said vinyl bromide by evaporation to leave in susbtantially pure isolated form said butyric acid and/or said n-butanol.

2. The process of claim 1 wherein said broth is adjusted to a pH within the range of from about 3.5 to about 4.0.

3. A process of extracting butyric acid and/or n-butyl alcohol from microbial fermentation broth containing the same, said process comprising:

acidifying a microbial fermentation broth containing butyric acid and/or n-butanol to a pH within the range of from about 4.0 to about 3.5;

introducing said acidified fermentation broth into the bottom of a series of extraction columns containing vinyl bromide maintained at a temperature of from about 4° C. to about 15° C.;

withdrawing said fermentation broth from the tops of said columns; and evaporating the vinyl bromide to leave a residue of butyric acid and n-butanol.

4. The process of claim 3 wherein said evaporated vinyl bromide is condensed and reintroduced into said colums.

5. The process of claim 4 wherein said process is a continuous process.

6. The process of claim 3 wherein the number of columns in said series is from about 3 to about 8.

7. The process of claim 6 wherein the number of columns is from about 4 to about 7.

* * * * *